US006440954B1

(12) United States Patent
Haber et al.

(10) Patent No.: US 6,440,954 B1
(45) Date of Patent: Aug. 27, 2002

(54) INHIBITION OF VASCULAR SMOOTH MUSCLE CELL PROLIFERATION

(75) Inventors: Carol Haber, Salisbury, NH (US), executrix of said Edgar Haber deceased; Wen-Sen Lee, Taipei (TW)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 09/061,609

(22) Filed: Apr. 16, 1998

Related U.S. Application Data

(60) Provisional application No. 60/044,651, filed on Apr. 18, 1997.

(51) Int. Cl.[7] .................. A61K 31/56; G01N 33/53; C07K 14/00; C07J 1/00
(52) U.S. Cl. .................. 514/169; 514/177; 514/2; 435/7.21; 435/375; 435/377; 530/300; 530/350; 530/399
(58) Field of Search .................. 435/7.21, 375, 435/377, 383; 514/2, 177, 169; 530/300, 350, 399

(56) References Cited

U.S. PATENT DOCUMENTS

| 5,366,862 A | 11/1994 | Venton et al. ............ 435/7.1 |
| 5,516,528 A | 5/1996 | Hughes et al. ............ 424/464 |
| 5,580,722 A | 12/1996 | Foulkes et al. ............ 435/6 |

FOREIGN PATENT DOCUMENTS

| WO | WO 94/05268 | 3/1994 |
| WO | WO 94/24080 | 10/1994 |
| WO | WO 95/11973 | 5/1995 |

OTHER PUBLICATIONS

Bagchi et al., "Ligand and DNA–dependent Phosphorylation of Human Progesterone Receptor In Vitro," *Proc. Natl. Acad. Sci. USA*, 89:2664–2668, 1992.
Denner et al., "Regulation of Progesterone Receptor–Mediated Transcription by Phosphorylation," *Science*, 250:1740–1743, 1990.
El–Ashry et al., "Human Progesterone Receptor Complexed With The Antagonist RU 486 Binds To Hormone Response Elements In A Structurally Altered Form," *Molecular Endocrinology*, 3:1545–1558, 1989.
Farhat et al., "In Vitro Effect Of Oestradiol On Thymidine Uptake In Pulmonary Vascular Smooth Muscle Cell: Role Of The Endothelium," *British Journal Pharmacology*, 107:679–683, 1992.
Grodstein et al., "Postmenopausal Estrogen And Progestin Use And The Risk Of Cardiovascular Disease," *The New England Journal of Medicine*, 335:453–461, 1996.
Guiochon–Mantel et al., "Mechanisms Of Nuclear Localization Of The Progesterone Receptor: Evidence For Interaction Between Monomers," *Cell*, 57:1147–1154, 1989.

Ingegno et al., "Progesterone Receptors In The Human Heart And Great Vessels," *Laboratory Investigation*, 59:353–356, 1988.
Klein–Hitpass et al., "The Progesterone Receptor Stimulates Cell–Free Transcription By Enhancing The Formation Of A Stable Preinitiation Complex," *Cell*, 60:247–257, 1990.
Knauthe et al., "Sexual Dimorphism Of Steriod Hormone Receptor Messenger Ribonucleic Acid Expression And Hormonal Regulation In Rat Vascular Tissue," *Endocrinology*, 137:3220–3227, 1996.
Kushwaha et al., "Effects Of Estrogen And Progesterone On Plasma Lipoproteins And Experimental Atherosclerosis In The Baboon (Papio sp.)," *Arteriosclerosis and Thrombosis*, 11:23–31, 1991.
McGill et al., "Sex and Atherosclerosis," *Atherosclerosis Reviews*, 4:157–242, 1979.
Pfahl, "Specific Binding Of The Glucocorticoid–Receptor Complex To The Mouse Mammary Tumor Proviral Promoter Region," *Cell*, 31:475–482, 1982.
Sherr, "Mammalian $G_1$ Cyclins," *Cell*, 73:1059–1065, 1993.
Stamler et al., "Prevention Of Coronary Atherosclerosis By Estrogen–Androgen Administration In The Cholesterol–Fed Chick," *Circulation Research*, 1:94–98, 1953.
Stampfer et al., "Postmenopausal Estrogen Therapy And Cardiovascular Disease," *The New England Journal Of Medicine*, 325:756–762, 1991.
Sullivan et al., "Estrogen Inhibits The Response–to–Injury In A Mouse Carotid Artery Model," *J. Clin. Invest.*, 96:2482–2488, 1995.
Tsai et al., "Promotion Of Vascular Smooth Muscle Cell Growth By Homocysteine: A Link To Atherosclerosis," *Proc. Natl. Acad. Sci. USA*, 91:6369–6373, 1994.
Vegeto et al., "The Mechanism Of RU486 Antagonism Is Dependent On The Conformation Of The Carboxy–Terminal Tail Of The Human Progesterone Receptor," *Cell*, 69:703–713, 1992.
Weigensberg et al., "Effects Of Estradiol On Myointimal Thickenings From Catheter Injury And On Organizing White Mural Non–occlusive Thrombi," *Atherosclerosis*, 52:253–265, 1984.
The Writing Group for the PEPI Trial, "Effects of Estrogen or Estrogen/Progestin Regimens on Hear Disease Risk Factors in Postmenopausal Women," *JAMA*, 273:199–208, 1995.
Yoshizumi et al., "Disappearance of Cyclin A Correlates With Permanent Withdrawal Of Cardimyocytes From The Cell Cycle In Human And Rat Heads," *J. Clin. Invest.*, 95:2275–2280, 1995.

*Primary Examiner*—Yvonne Eyler
*Assistant Examiner*—Nirmal S. Basi
(74) *Attorney, Agent, or Firm*—Ingrid A. Beattie; Mintz Levin Cohn Ferris Glovsky & Popeo, PC

(57) ABSTRACT

Methods of treating a mammal having a condition characterized by vascular smooth muscle cell proliferation, where the mammal is treated with progesterone or an agonist thereof. Also disclosed are methods of screening compounds useful for inhibiting vascular smooth muscle cell proliferation.

11 Claims, 5 Drawing Sheets

INHIBITION OF VASCULAR SMOOTH MUSCLE CELL PROLIFERATION

CROSS REFERENCE TO RELATED APPLICATIONS

Under 35 USC §119(e)(1), this application claims the benefit of prior U.S. provisional application Ser. No. 60/044,651, filed Apr. 18, 1997.

STATEMENT AS TO FEDERALLY SPONSORED RESEARCH

The invention was funded in part by National Institutes of Health Grant RO1GM 53249. The government has certain rights in the invention.

FIELD OF THE INVENTION

This invention relates to cardiovascular disease.

BACKGROUND OF THE INVENTION

Cardiovascular disease, the principal cause of death in the developed world, affects men far more frequently than premenopausal women of the same age. Because the incidence of cardiovascular disease in postmenopausal women gradually approaches that in age-matched men (McGill et al., *Atheroscler. Rev.* 4, 157–242 (1979)), estrogen or progesterone appears to have a protective effect in premenopausal women. A large, 10-year prospective study supports such a cardioprotective effect of estrogen by showing that postmenopausal estrogen-replacement therapy reduces both the incidence of coronary heart disease and mortality from cardiovascular disease (Stampfer, M. J. et al., *N. Engl. J. Med.* 325, 756–762 (1991)).

As for the effects of progesterone on cardiovascular disease, however, there has been little information until the recent report by Grodstein et al. (*N. Engl. J. Med.* 335, 453–461 (1996)) showing that the risk of coronary heart disease is significantly lower in women who take estrogen and progesterone together rather than estrogen alone. Estrogen administration inhibits the development of experimentally induced atherosclerosis in rodent models (Stamler et al., *Circ. Res.* 1, 94–98 (1953); Weigensberg et al., *Atherosclerosis* 52, 253–265 (1984); and Sullivan et al., *J. Clin. Invest.* 96, 2482–2488 (1995)). Also, in castrated baboons receiving estradiol and progesterone together, there are fewer vascular lesions than in those receiving estradiol alone (Kushwaha et al., *Arterioscler. Thromb.* 11, 23–31 (1991)). However, there is little evidence of an independent effect of progesterone in animal studies or in cell culture.

Current methods of treating severe cardiovascular conditions, such as coronary stenosis and occlusion caused by atherosclerosis, include invasive cardiovascular surgical procedures [e.g., percutaneous translumenal coronary angioplasty ("PTCA") and aorta-coronary bypass surgery ("ACBS")]. However, the cellular proliferative response and associated intimal hyperplasia that may follow the damage to blood vessels caused by these procedures leads to complications which cannot be effectively controlled by presently available drugs, and can therefore be more detrimental than the original condition. The development of these complications, termed restenosis (in the case of PTCA) or stenosis (in the case of ACBS), has similarities to the development of atherosclerosis.

SUMMARY OF THE INVENTION

The invention is based on Applicants' discovery that (1) progesterone has a direct and specific inhibitory effect on arterial smooth muscle cell proliferation; (2) this inhibition occurs at a progesterone concentration that overlaps the physiological range of progesterone concentrations in the plasma of premenopausal women; (3) arterial smooth muscle cells contain abundant progesterone receptors ("PgR") that mediate this effect; and (4) in the presence of progesterone, mRNA levels of cyclins A and E decline in rat arterial smooth muscle cells ("RASMC"), suggesting that progesterone interrupts the cell cycle at the G1/S transition. To Applicants' knowledge, this is the first demonstration that progesterone exerts a direct inhibitory effect on vascular smooth muscle cell proliferation.

Applicants' discovery provides a biochemical explanation for the recent epidemiological observation that the relative risk of major coronary heart disease was 0.39 in postmenopausal women who took estrogen with progesterone, as compared with a risk of 0.60 in those who took estrogen alone (where the risk among women who took no hormones was set at 1.0) (Grodstein et al, supra).

Accordingly, the present invention features a method of treatment. In this method, one first identifies a mammal that is suspected of having, or at a risk of having, a condition characterized by vascular smooth muscle cell ("VSMC") proliferation and that is not being treated with estrogen or an estrogen agonist. Such a mammal can, for example, be a mouse, rat, dog, cat, cow, pig, horse, goat, sheep, rabbit, guinea pig, hamster or primate, such as a an adult human (e.g., a man, a premenopausal woman, or a postmenopausal woman who is not presently on an estrogen replacement therapy). A mammal is at a risk of having the condition when it, for example, is at an age of being susceptible to the condition, or is genetically predisposed to or has a family history of the condition, or is about to undergo or has recently undergone vascular surgery. A condition marked by VSMC proliferation is typically a cardiovascular or coronary heart disease such as transplant arteriosclerosis, atherosclerosis, angioplasty restenosis, or cardiac vein bypass stenosis.

After such a mammal is identified, one can then administer to the mammal progesterone or a progesterone agonist in an amount effective to decrease VSMC proliferation in the mammal. A progesterone agonist is a compound that mimics, to various degrees, the effects of progesterone. This compound can be, for instance, an organic compound, a peptide, or a nucleic acid.

An amount of progesterone or an agonist thereof is effective when its administration results in inhibition of VSMC proliferation in a blood vessel in the mammal.

Also embraced by the invention are methods of identifying compounds potentially useful for inhibiting VSMC proliferation. In these methods, a test compound is contacted with a progesterone receptor (PgR). There are at least two isoforms of PgRs: PgR A and PgR B, the molecular weights of which are approximately 94 and 114 kD, respectively. The test compound's binding to the PgR is an indication that the compound is potentially useful for inhibiting vascular smooth muscle cell proliferation. The PgR can be in a purified protein preparation, in a cellular extract, or inside cells [e.g., VSMCs or cells (e.g., mammalian, yeast, insect, or bacterial cells) that have been transfected with a DNA construct directing expression of the PgR].

Alternatively, the potential usefulness of a test compound is indicated by its ability to activate the PgR in a cell or in a cell extract. Activation of the PgR is detected, for example, by the phosphorylation status of the PgR, or by enhanced transcription of a gene that is linked to a cis progesteroneresponsive DNA element (e.g., the hormone response element of the mouse mammary tumor virus). This gene can be an endogenous gene such as cyclin A or E, whose transcription is downregulated by activated progesterone receptors (see Example, infra). Alternatively, the gene is an exogenously introduced reporter gene whose expression can be readily determined by a biochemical assay (e.g., a gene that encodes a firefly luciferase, β-galactosidase, or alkaline phosphatase) or by drug resistance of the cell harboring the gene (e.g., a gene that encodes chloramphenicol acetyltransferase, neomycin phosphotransferase, or guanine xanthine phosphoribosyltransferase).

The invention also provides methods of determining whether compounds known or suspected to bind a PgR, such as known progesterone agonists (e.g., norethisterone, or norgestrel), are potentially useful for inhibiting VSMC proliferation. In these methods, mammalian cells (e.g., mammalian VSMCs) containing a PgR are incubated with the compounds and relative proliferation of the cells is determined (e.g., by the amount of radioactive nucleotides incorporated into replicating genomic DNA, or by the number of cells generated by cell division). The potential usefulness of PgR-binding compounds can also be determined by measuring their ability to decrease cyclins A and/or E activity or expression level (e.g., amounts of proteins or mRNA transcripts) in mammalian cells (e.g., mammalian VSMCs) containing a PgR.

Cells used to practice the invention can be freshly isolated from tissues or cultured from isolated tissue cells. The cells can also be those that have been immortalized in vivo (i.e., cancer cells) or in vitro. A PgR used in the invention can be either naturally occurring (i.e., encoded by an endogenous gene) or recombinant, and need not be full length, so long as it contains the domains essential for its functions.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can be used in the practice or testing of the present invention. All publications and other references mentioned herein are incorporated by reference in their entirety. In case of conflict, the present specification, including definitions, will control. The materials, methods, and examples are illustrative only and not intended to be limiting.

Other features and advantages of the invention will be apparent from the following detailed description, and from the claims.

BRIEF DESCRIPTION OF THE DRAWINGS

FIGS. 1a–c show sequential sections of arterial tissue from a premenopausal woman. In FIG. 1a, a number of nuclei were positively stained for the PgR (black spots, filled arrow), but some (open arrow) showed no PgR immunoreactivity. In FIG. 1b, the absence of black spots after preabsorption with the PgR antigen demonstrates the specificity of the anti-PgR antibody staining. FIG. 1c shows that, in tissue double-stained for the PgR and α-actin (pink), PgRs localized to HASMCs. In FIG. 1d, a number of nuclei were also positively stained for the PgR in a rat arterial tissue section. In FIGS. 1e and f, PgRs and α-actin colocalized in cultured HASMCs and RASMCs, respectively.

FIG. 2a, Dose-dependent inhibition of [$^3$H]thymidine incorporation in RASMCs by progesterone. FIG. 2b, Progesterone-induced inhibition of [$^3$H]thymidine incorporation blocked by the PgR antagonist RU486. FIG. 2c, Effect of FCS concentration on inhibition of [$^3$H]thymidine incorporation induced by progesterone at 500 nM. FIG. 2d, Dose-dependent inhibition of [$^3$H]thymidine incorporation in HASMCs by progesterone. Results from representative experiments are shown. Four samples were analyzed in each experiment, and values represent the (mean±SEM). Comparisons were subjected to ANOVA followed by Fisher's least significant difference test. Significance was accepted at $P<0.05$. *, Progesterone-treated group different from control group (100%). §, Progesterone-treated group different from RU486-treated group and RU486+progesterone-treated group.

DETAILED DESCRIPTION OF THE INVENTION

The invention provides a method of treating a mammal with progesterone or a progesterone agonist. Any known progesterone agonist is a candidate for use in this treatment method; the efficacy of the agonist compound can be tested in vitro using the methods of the invention and/or in vivo using animal models.

Progesterone or its agonist can be administered alone or in a pharmaceutically acceptable carrier (e.g., physiological saline), which is selected on the basis of the mode and route of administration, and standard pharmaceutical practice. Suitable pharmaceutical carriers, as well as pharmaceutical necessities for use in pharmaceutical formulations, are described in Remington's Pharmaceutical Sciences, a standard reference text in this field, and in the USP/NF. Progesterone or its agonists can be administered in dosages determined to be appropriate by one skilled in the art. It is expected that the dosages will vary, depending upon the pharmacokinetic and pharmacodynamic characteristics of the particular agent, and its mode and route of administration, as well as the age, weight, and health of the recipient; the nature and extent of the disease; the frequency and duration of the treatment; the type of, if any, concurrent therapy; and the desired effect. It is expected that a useful dosage contains between about 0.1 to 100 mg of active ingredient per kilogram of body weight. Ordinarily, 0.5 to 50 mg, and preferably 1 to 10 mg of active ingredient (e.g., a progestin) per kilogram of body weight per day, given in divided doses or in sustained release form, is appropriate. The compound may be administered to a patient by any appropriate mode, e.g., orally, transmucosally, transdermally, subcutaneously, intramuscularly, or intravenously, as determined by one skilled in the art. Implants which deliver a steady low dosage over a long period of time are particularly desirable. Appropriate types of formulations for each of such delivery routes are well known, or can be derived using standard methods.

Described below is evidence that progesterone can inhibit VSMC proliferation. The experimental procedures and data are meant to illustrate, but not limit, the methods of the invention. Other suitable modifications and adaptations of the variety of conditions and parameters of the following procedures are within the spirit and scope of the present invention.

Experimental Data

Materials and Methods
Immunocytochemistry

Figure 1A:
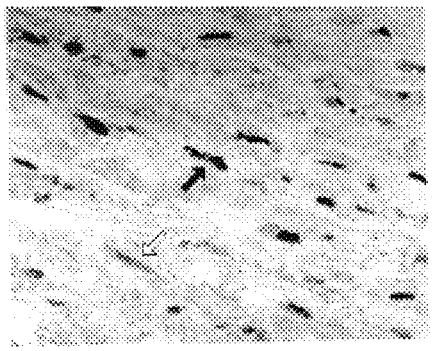
FIGS. 1a–f are a set of photographs showing localization of PgRs in human arterial smooth muscle cells ("HASMC"s) and rat arterial smooth muscle cells ("RASMC"s) (original magnification: 400×).
Figure 1B:
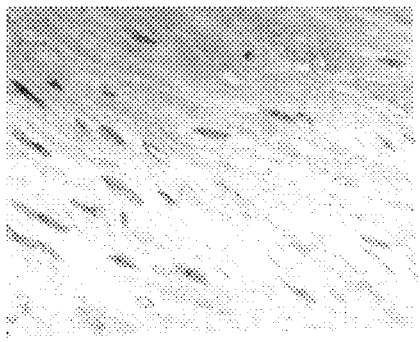
Figure 2A:
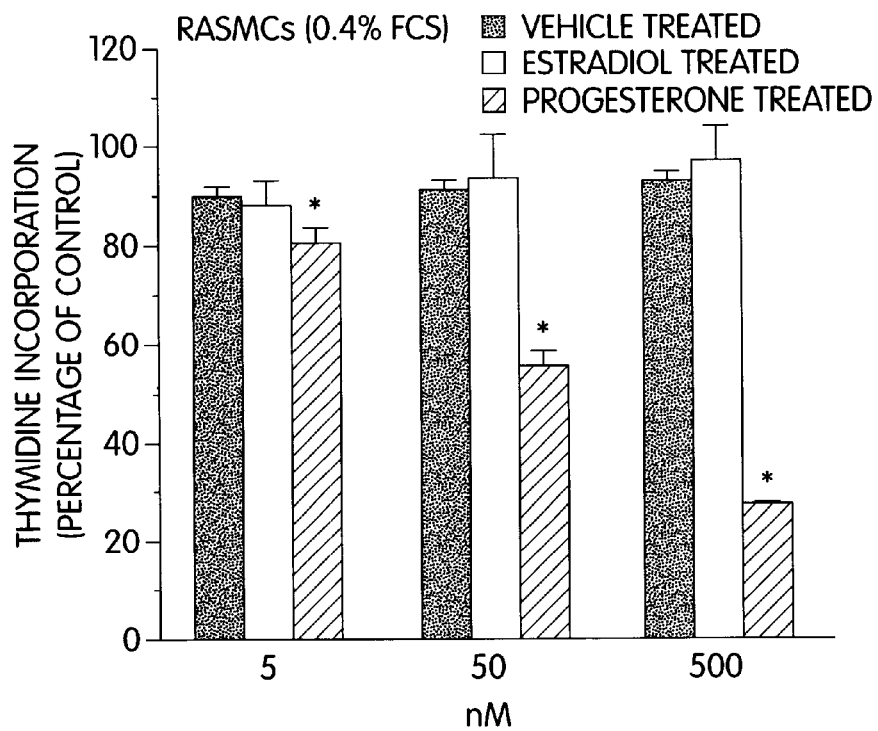
FIGS. 2a–2d are graphs showing effect of progesterone on [$^3$H]thymidine incorporation in RASMCs or HASMCs. Thymidine incorporation is expressed as a percentage of the value for the control (PBS-treated) group (100%).
Figure 2B:
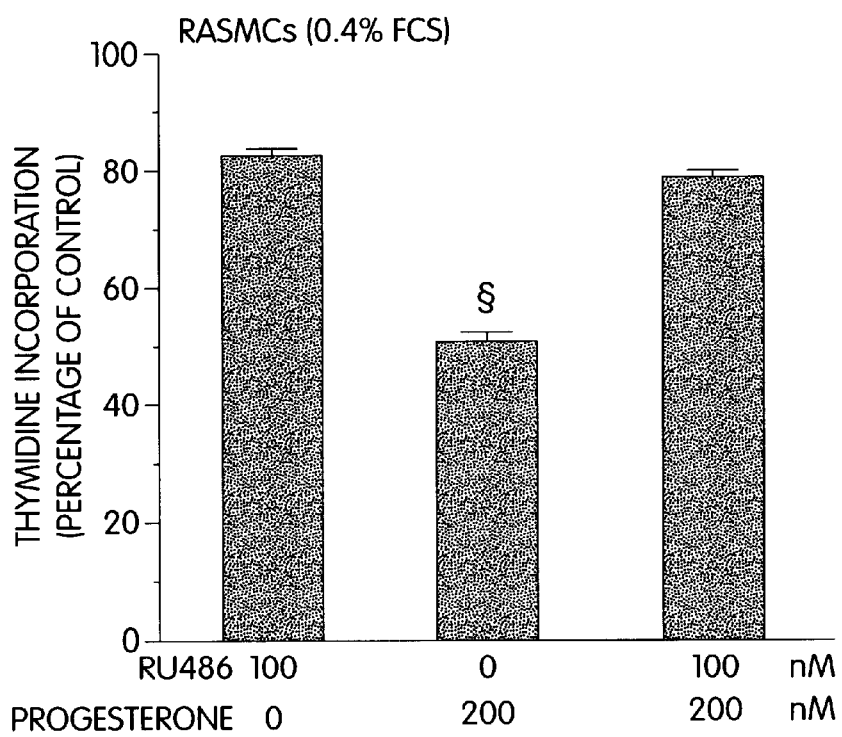
Figure 2C:
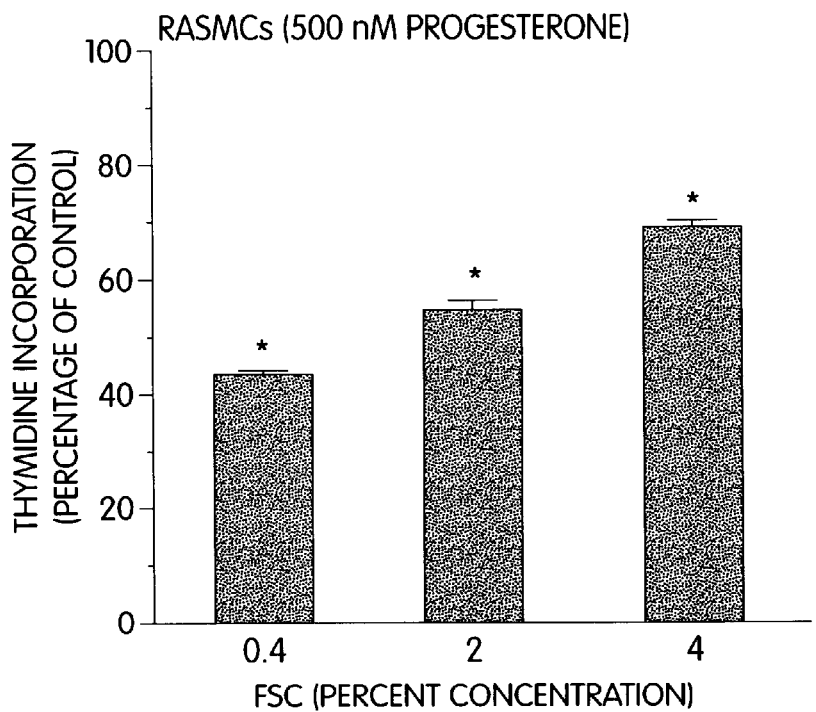

Adult female rat aortas were fixed in 4% paraformaldehyde. The aorta from a premenopausal woman (provided by the Beth Israel Hospital, Boston) was fixed in 10% formalin. The aortas were processed for paraffin embedding in an automated system (Hypercenter XP, Shandon Scientific Ltd) and cut at a thickness of 5 $\mu$m. Cultured RASMCs and HASMCs (grown on cover slips) were rinsed three times with PBS, fixed with phosphate-buffered 4% paraformaldehyde for 10 min, and then washed extensively with PBS. Immunocytochemical analysis for PgRs was performed as described (Lee et al., *Proc. Natl. Acad. Sci. USA* 87, 5163–5167 (1990); Yoshizumi et al., *J. Clin. Invest.* 95, 2275–2280 (1995)). Polyclonal rabbit anti-human PgR antibody [PR (C-20), Santa Cruz, Calif.] was applied at a 150 $\mu$g/$\mu$l dilution, and goat anti-rabbit secondary antibody (IgG H+L, Vector Laboratories, Burlingame, Calif.) was applied at a 1:200 dilution. To control for PgR specificity, arterial tissue (FIG. 1b) and cultured arterial smooth muscle cells (not shown) were also incubated with anti-PgR antibody that had been preabsorbed with the PgR antigen [40 $\mu$g/ml; PR (C-20 P), Santa Cruz, California]. PgR staining was developed by the avidin-biotin horseradish peroxidase (ABC) method, with 3,3'-diaminobenzidine/nickel sulfate used as chromogen to yield a black reaction product. Tissue was counter-stained with methyl green to visualize nuclei. Staining for $\alpha$-actin (a marker for smooth muscle cells) was visualized by an immunophosphatase technique, with alkaline phosphatase used as chromogen to yield a pink reaction product.
Cell Culture RASMCs were harvested from the thoracic aortas of adult male Sprague-Dawley rats (200–250 g) by enzymatic dissociation as described (Tsai et al., *Proc. Natl. Acad. Sci. USA* 91, 6369–6373 (1994)). The cells were grown in DMEM supplemented with 10% FCS, penicillin (100 U/ml), streptomycin (100 $\mu$g/ml), glutamine (200 nM), and 25 mM Hepes (pH 7.4) in a humidified incubator (37° C., 5% $CO_2$). HASMCs (Clonetics, San Diego) were grown in M199 medium (GIBCO BRL, Grand Island, N.Y.) supplemented with 20% FCS, penicillin (100 U/ml), streptomycin (100 $\mu$g/ml), and 25 mM Hepes (pH 7.4). Cells from passages 5–9 were used.
[$^3$H]thymidine Incorporation RASMCs and HASMCs were cultured in 24-well plates containing an appropriate growth medium (DMEM plus 10% FCS for RASMCs, and M199 plus 20% FCS for HASMCs). After the cells had grown to 70–80% confluence, they were rendered quiescent by incubation for 72 h in DMEM (for RASMCs) or M199 (for HASMCs) containing 0.4% charcoal/dextran-treated FCS (FIGS. 2a and 2d) or 0.4% calf serum (CS) (FIGS. 2b and 2c). Phenol red-free DMEM was used in the experiments with estradiol (FIG. 2a). Water-soluble progesterone (Sigma), estradiol (Sigma), 2-hydroxypropyl-$\beta$-cyclodextrin (vehicle used to make progesterone and estradiol water soluble; Sigma), or PBS (control) was added to the cells at various concentrations and the cells were incubated for an additional 24 h. In some cases (FIG. 2b), cells were treated with the progesterone receptor antagonist RU486 for 1 h and then incubated with progesterone for another 24 h. For determining the effects of serum concentration on progesterone-induced [$^3$H] thymidine incorporation (FIG. 2c), FCS in various concentrations was added right after the addition of progesterone. During the last 3 h of the 24-h incubation with progesterone, cells were labeled with [methyl-$^3$H]thymidine (DuPont-NEN, Boston, Mass.) at 1 $\mu$Ci/ml (1 $\mu$Ci=37 kBq). After incubation, the cells were washed with Dulbecco's PBS, fixed in cold 10% TCA for at least 2 h, and then washed with 95% ethanol. Incorporated [$^3$H]thymidine was extracted in 0.2 N NaOH and measured in a liquid scintillation counter.
Cell Counting RASMCs ($2\times10^4$) were seeded onto 6-well plates and grown in DMEM supplemented with 10% FCS. Twenty-four hours later, cells in one plate were released for counting (FIG. 3a, day 0) and the remaining plates were treated with fresh medium (DMEM supplemented with 1% or 2% charcoal/dextran-treated FCS) and progesterone (3 wells) or vehicle (3 wells). Medium and progesterone were changed daily. Cells were counted in a Coulter apparatus at various times after their removal from the plates with trypsin-EDTA.
Viability Assay RASMCs were applied to 24-well plates in growth medium (DMEM plus 10% FCS). After the cells had grown to 70–80% confluence, they were rendered quiescent by incubation for 72 h with DMEM containing 0.4% CS. A fresh medium (phenol red-free DMEM supplemented with 2% charcoal/dextran-treated FCS) was applied and a water soluble form of progesterone (Sigma) was added at 0, 5, 50, and 500 nM, and the cells were incubated for an additional 24 h. Cell viability was determined with a modified 3-(4,5-dimethyl thiazol-2-yl)-2,5-diphenyl tetrazolium bromide (MTT) assay, which is based on the conversion of the tetrazolium salt 3-(4,5-dimethyl thiazol-2-yl)-5-(3-carboxymethoxyphenyl)-2-(4-sulfophenyl)2-H-tetrazolium by the mitochondrial dehydrogenase to a formazan product, as measured at an absorbance of 490 nm. Four samples were analyzed in each experiment.
RNA Preparation and Northern Analysis Total RNA from RASMCs was prepared from cultured RASMCs by guanidinium isothiocyanate extraction and centrifugation through cesium chloride. Before RNA extraction, cells were made quiescent for 72 h with 0.4% CS and then incubated for 24 h with 2% charcoal/dextran-treated FCS and vehicle or various doses of progesterone. RNA samples (20 $\mu$g/lane) were electrophoresed on 1.3% formaldehyde-agarose gel, and then transferred onto nitrocellulose filters. The filters were hybridized to $^{32}$P-labeled human cyclin probes as described (Lee et al., *J. Biol. Chem.* 266, 16188–16192 (1991); Lee et al., *J. Biol Chem.* 269, 12032–12039 (1994)). To normalize RNA content of each lane, the filters were washed at 80° C. in 50% formamide solution to remove the cyclin probes, and then hybridized with oligonucleotide probes for 28S RNA. Hybridized filters were washed in 30 mM NaCl, 3 mM sodium citrate, and 0.1% sodium dodecyl sulfate at 55° C. Radioactive signals were visualized on Kodak XAR film or PhosphorImager screens (Molecular Dynamics, Inc. Sunnyvale, Calif.).

Results

Vascular Smooth Muscle Cells Express the Progesterone Receptor

Figure 1C:
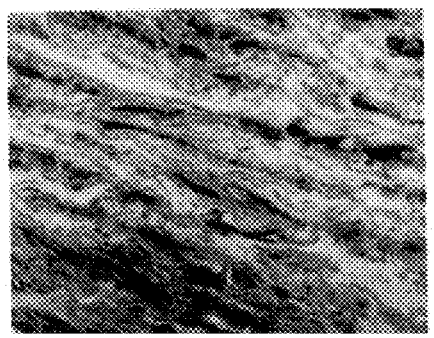
Figure 1D:
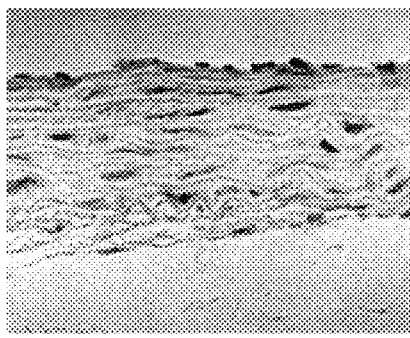
Figure 1E:
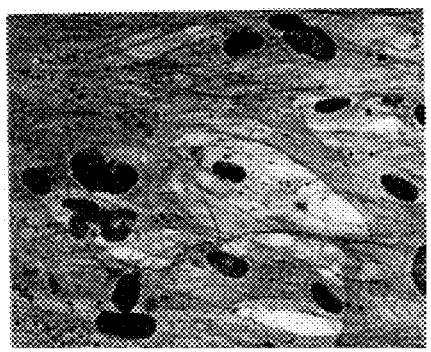
Figure 1F:
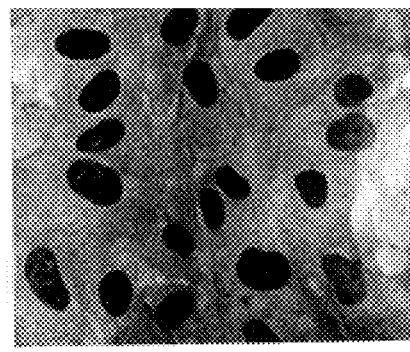

The presence of PgRs in the medial layer of the aorta (Ingegno et al., *Lab. Invest.* 59, 353–356 (1988)) suggests that they are expressed by HASMCs. To confirm that such PgR-positive cells are indeed smooth muscle cells, we double-stained human and rat tissue, cultured HASMCs, and RASMCs for PgRs and α-actin (a marker of smooth muscle cells). PgR-positive nuclei appeared in the medial layer of an arterial tissue section from a premenopausal woman (FIG. 1a), and the staining was blocked in a sequential section treated with anti-PgR antibody that had been preabsorbed with PgR antigen (FIG. 1b). In another sequential section (FIG. 1c), PgR-positive nuclei (black) colocalized with α-actin-positive cells (pink). PgR-positive nuclei were also present in the medial layer of a section of rat arterial tissue (FIG. 1d). In culture, HASMCs (FIG. 1e) and RASMCs (FIG. 1f) both expressed PgRs in their nuclei.

Figure 2D:
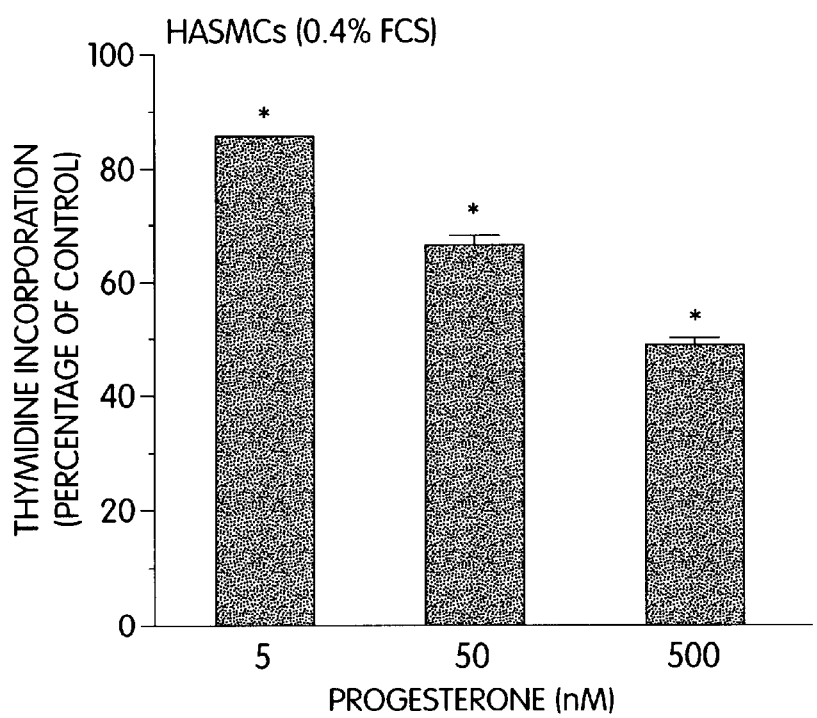

Progesterone Inhibits [$^3$H]Thymidine Incorporation in Arterial Smooth Muscle Cells Changes in [$^3$H]thymidine incorporation in response to progesterone were next examined in RASMCs and HASMCs. Progesterone, but not estradiol or 2-hydroxypropyl-β-cyclodextrin (the vehicle in which the progesterone and estradiol were made water soluble), inhibited [$^3$H]thymidine incorporation in RASMCs (FIG. 2a), and this inhibition was dose-dependent. To confirm the specificity of progesterone's inhibitory effect on [$^3$H] thymidine incorporation, we preincubated RASMCs with the progesterone receptor antagonist RU486. Although RU486 by itself had little effect on [$^3$H]thymidine incorporation, it antagonized the inhibition of [$^3$H]thymidine incorporation induced by progesterone (FIG. 2b). The inhibitory effect of progesterone on RASMCs could be counteracted by serum in a dose-dependent manner (FIG. 2c). A progesterone-induced, dose-dependent inhibition of [$^3$H]thymidine incorporation also occurred in HASMCs (FIG. 2d).

Progesterone Inhibits Arterial Smooth Muscle Cell Proliferation

Figure 3A:
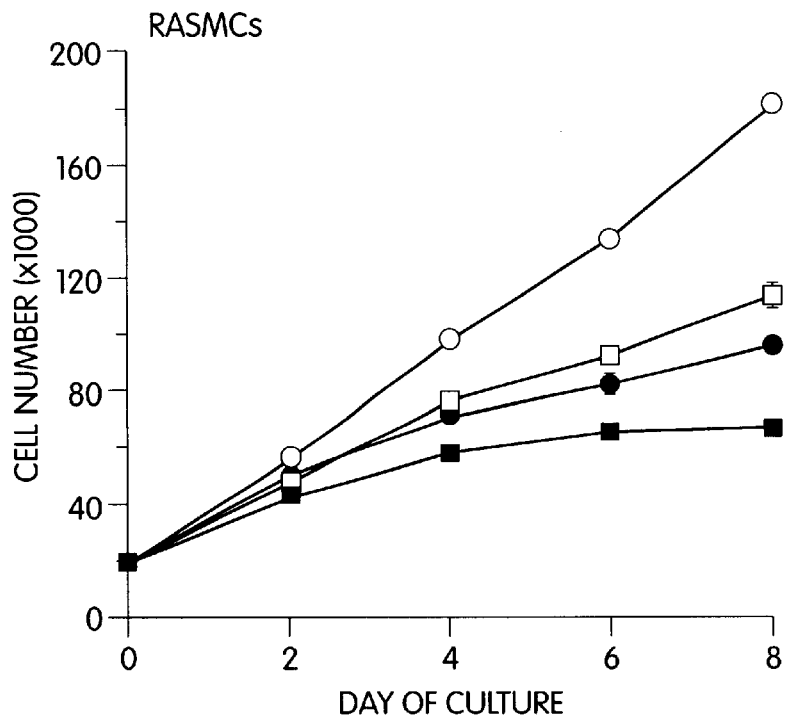
FIG. 3a is a graph showing the effect of progesterone on RASMC proliferation. Progesterone was added at 500 nM to Dulbecco's modified Eagle's medium ("DMEM") supplemented with 1% (filled squares) or 2% (filled circles) charcoal/dextran-treated fetal calf serum ("C/D FCS"). Vehicle was added also at 500 mM to DMEM supplemented with 1% (open squares) or 2% (open circles) C/D FCS.
Figure 3B:
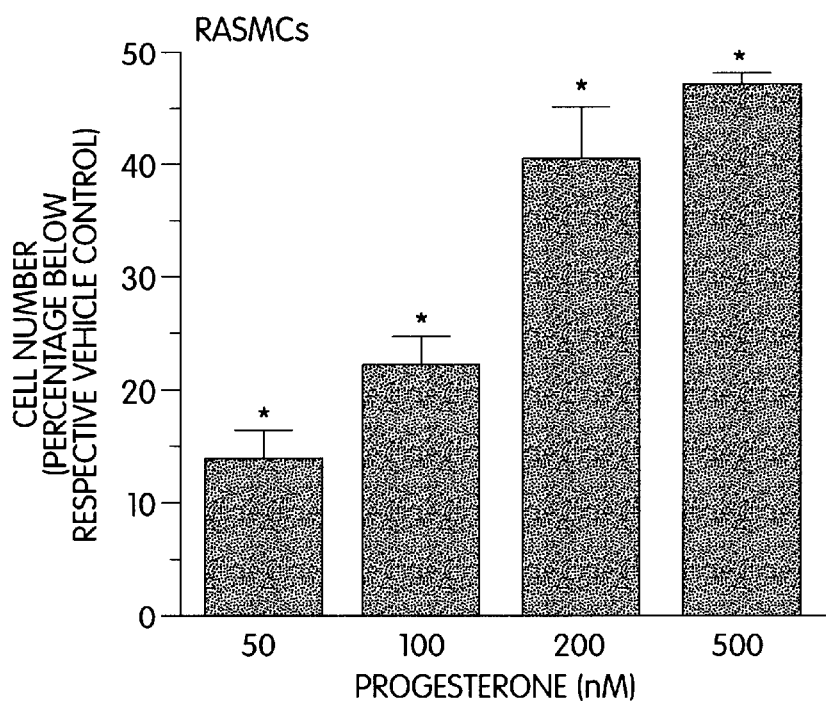
FIG. 3b is a graph showing the dose-dependent inhibition of RASMC growth by progesterone. Three samples were analyzed in each experiment. Values represent the mean± SEM. Comparisons were subjected to ANOVA followed by Fisher's least significant difference test. Significance was accepted at $P<0.05$. *, Progesterone-treated group different from respective vehicle control group (100%).

To confirm further that progesterone inhibits smooth muscle cell proliferation, the effect of progesterone on the growth rate of RASMCs was examined. At FCS concentrations of 1% and 2%, the growth of RASMCs treated with progesterone (500 nM) decreased in comparison with cells treated with vehicle (500 nM) (FIG. 3a). Cell numbers diverged by the second day of culture; and at day 8, the number of progesterone-treated RASMCs was only 40–50% of that of vehicle-treated cells (FIG. 3a). This progesterone-induced reduction in cell growth was also dose-dependent (FIG. 3b), and was consistent with the inhibitory effect of progesterone on [$^3$H]thymidine incorporation.

To confirm that the inhibition of DNA synthesis and cell proliferation by progesterone was not due to cell death caused by progesterone treatment, a viability assay was conducted. No significant difference in viability between vehicle-treated and progesterone-treated RASMCs (at progesterone concentrations of 0, 5, 50, or 500 nM) was observed.

Figure 4:
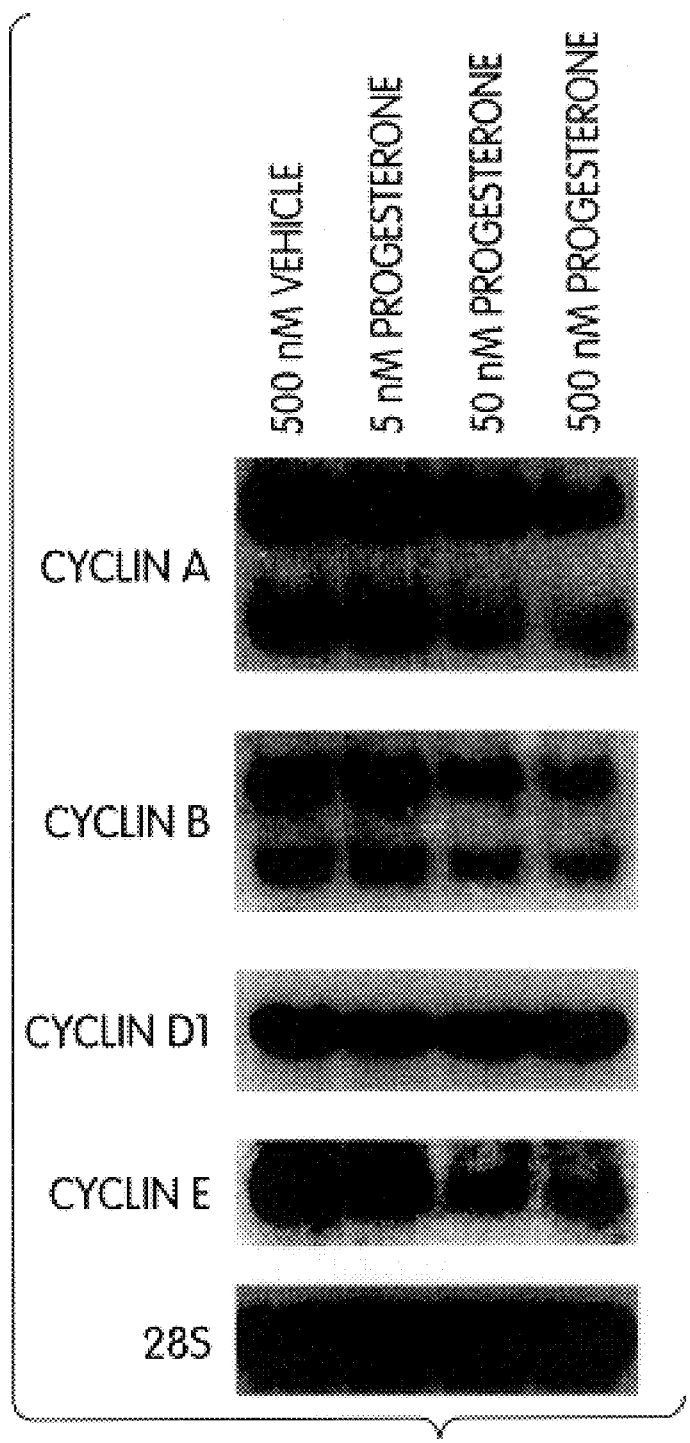
FIG. 4 is a set of autoradiographs showing Northern blot analysis of cyclin mRNAs expressed in the presence of the indicated doses of progesterone.

Progesterone Downregulates Expression of Cyclin A and E mRNAs in Arterial Smooth Muscle Cells Progression of the cell cycle is regulated by the sequential expression of cyclins. To determine the effect of progesterone on cyclin expression, cyclin mRNAs in RASMCs were examined. Twenty-four hours after progesterone treatment, the levels of cyclin A and E mRNAs were downregulated (FIG. 4). In contrast, the levels of cyclins B and D1 mRNA did not change. These data suggest that progesterone may inhibit arterial smooth muscle cell proliferation by interrupting the cell cycle at the G1/S transition.

OTHER EMBODIMENTS

It is to be understood that while the invention has been described in conjunction with the detailed description thereof, the foregoing description is intended to illustrate and not to limit the scope of the invention, which is defined by the scope of the appended claims.

Other aspects, advantages, and modifications are within the scope of the following claims.

What is claimed is:

1. A method of treatment comprising:
   identifying a mammal that is suspected of having, or at risk of having, a condition characterized by vascular smooth muscle cell proliferation and that is not being treated with estrogen or an agonist thereof; and
   administering to the mammal, an amount of progesterone effective to decrease vascular smooth muscle cell proliferation in the mammal, wherein said condition is selected from the group consisting of transplant arteriosclerosis, atherosclerosis, and angioplasty restenosis, aorta-coronary bypass stenosis.

2. The method of claim 1, wherein the mammal is a man or a premenopausal woman.

3. The method of claim 1, wherein the condition is transplant arteriosclerosis.

4. The method of claim 1, wherein the condition is atherosclerosis.

5. The method of claim 1, wherein the condition is angioplasty restenosis.

6. The method of claim 1, wherein said condition is aorta-coronary bypass stenosis.

7. A method of inhibiting proliferation of a mammalian vascular smooth muscle cell, comprising contacting said cell with progesterone in the absence of estrogen or an agonist thereof.

8. The method of claim 7, wherein said cell is from a man, premenopausal woman, or a postmenopausal woman who is not on estrogen replacement therapy.

9. The method of claim 7, wherein said cell is an arterial smooth muscle cell.

10. The method of claim 7, wherein said cell is an aortic smooth muscle cell.

11. The method of claim 7, wherein said cell is a thoracic aortic smooth muscle cell.

* * * * *

UNITED STATES PATENT AND TRADEMARK OFFICE
CERTIFICATE OF CORRECTION

| | | |
|---|---|---|
| PATENT NO. | : 6,440,954 B1 | Page 1 of 1 |
| APPLICATION NO. | : 09/061609 | |
| DATED | : August 27, 2002 | |
| INVENTOR(S) | : Haber et al. | |

It is certified that error appears in the above-identified patent and that said Letters Patent is hereby corrected as shown below:

In the Specification

At Column 1, Line number 13, please delete the paragraph labeled "STATEMENT AS TO FEDERALLY SPONSORED RESEARCH" and replace it with the following paragraph:
This invention was made with government support under GM053249 awarded by the National Institutes of Health. The government has certain rights in the invention.

Signed and Sealed this
Thirty-first Day of December, 2024

Derrick Brent
*Acting Director of the United States Patent and Trademark Office*